United States Patent
Sun et al.

(10) Patent No.: US 11,369,415 B2
(45) Date of Patent: Jun. 28, 2022

(54) RETRIEVABLE PUNCTURE ANCHOR

(71) Applicants: SHENGJING HOSPITAL OF CHINA MEDICAL UNIVERSITY, Liaoning (CN); JIANGSU VEDKANG MEDICAL SCIENCE & TECHNOLOGY CO., LTD, Jiangsu (CN)

(72) Inventors: Siyu Sun, Liaoning (CN); Donglin Miao, Jiangsu (CN)

(73) Assignee: SHENGJING HOSPITAL OF CHINA MEDICAL UNIVERSITY, Liaoning (CN)

( * ) Notice: Subject to any disclaimer, the term of this patent is extended or adjusted under 35 U.S.C. 154(b) by 166 days.

(21) Appl. No.: 16/870,187

(22) Filed: May 8, 2020

(65) Prior Publication Data
US 2020/0268414 A1    Aug. 27, 2020

Related U.S. Application Data

(63) Continuation of application No. PCT/CN2018/078686, filed on Mar. 12, 2018.

(30) Foreign Application Priority Data

Nov. 9, 2017 (CN) .......................... 201711096960.2

(51) Int. Cl.
*A61B 17/34* (2006.01)
*A61B 17/04* (2006.01)
(Continued)

(52) U.S. Cl.
CPC ...... *A61B 17/3478* (2013.01); *A61B 17/0401* (2013.01); *A61B 90/17* (2016.02);
(Continued)

(58) Field of Classification Search
CPC ........ A61B 17/0401; A61B 2017/0438; A61B 2017/0445; A61B 2017/0446;
(Continued)

(56) References Cited

U.S. PATENT DOCUMENTS

| 5,123,914 A | 6/1992 | Cope |
| 2007/0198017 A1 | 8/2007 | Tschakaloff et al. |

(Continued)

FOREIGN PATENT DOCUMENTS

| CN | 103932792 | 7/2014 |
| CN | 107714117 | 2/2018 |

(Continued)

OTHER PUBLICATIONS

Extended European Search Report from related EPO Appln. No. 18875310.7, dated Nov. 19, 2020.
(Continued)

*Primary Examiner* — Ashley L Fishback
(74) *Attorney, Agent, or Firm* — Grossman, Tucker, Perreault & Pfleger, PLLC

(57) ABSTRACT

A retrievable puncture anchor includes a fixator with a cylindrical structure, a retrievable thread secured to one end of the fixator, and a push cable flexibly connected to a middle part of the fixator. Via the retrievable puncture anchor, tissues may be connected, fixed and matched with each other, or the tissues may be auxiliarily fixed, so that endoscopic surgery may be facilitated with simplified surgical process, and the puncture anchor may be retrieved after the surgery.

9 Claims, 4 Drawing Sheets

(51) Int. Cl.
*A61B 90/17* (2016.01)
*A61B 17/00* (2006.01)

(52) U.S. Cl.
CPC ............... *A61B 2017/00296* (2013.01); *A61B 2017/00323* (2013.01); *A61B 2017/0414* (2013.01); *A61B 2017/0417* (2013.01); *A61B 2017/0438* (2013.01); *A61B 2017/0464* (2013.01); *A61B 2017/3454* (2013.01); *A61B 2017/3488* (2013.01)

(58) Field of Classification Search
CPC .... A61B 2017/0458; A61B 2017/0459; A61B 2017/0464; A61B 2017/0414; A61B 2017/0417; A61B 90/17
See application file for complete search history.

(56) References Cited

U.S. PATENT DOCUMENTS

| | | |
|---|---|---|
| 2008/0154097 A1 | 6/2008 | De La Torre et al. |
| 2016/0007987 A1 | 1/2016 | Catanese, III et al. |
| 2016/0144066 A1* | 5/2016 | Long .................... A61L 17/10 606/232 |

FOREIGN PATENT DOCUMENTS

| | | |
|---|---|---|
| EP | 0246836 | 11/1987 |
| WO | 02/087413 | 11/2002 |
| WO | 2005/112788 | 12/2005 |
| WO | 2015/058325 | 4/2015 |

OTHER PUBLICATIONS

English translation of the International Search Report from corresponding PCT Appln. No. PCT/CN2018/078686, dated Jul. 24, 2018.
English translation of the Written Opinion of the International Searching Authority from corresponding PCT Appln. No. PCT/CN2018/078686, dated Jul. 24, 2018.
English translation of First Office Action & Search Report from corresponding Chinese Appln No. 201711096960.2, dated Oct. 15, 2018.
English translation of Second Office Action & Search Report from corresponding Chinese Appln. No. 201711096960.2, dated Apr. 29, 2019.
English translation of Third Office Action & Search Report from corresponding Chinese Appln. No. 201711096960.2, dated Jul. 30, 2019.
English translation of Rejection Notice from corresponding Chinese Appln. No. 201711096960.2, dated Sep. 25, 2019.

* cited by examiner

RETRIEVABLE PUNCTURE ANCHOR

CROSS-REFERENCE TO RELATED APPLICATION

The present application is a by-pass continuation of PCT Application No. PCT/CN2018/078686, filed Mar. 3, 2018 and claims priority to Chinese Patent Application No. 201711096960.2, filed on Nov. 9, 2017, both of which are incorporated herein, by reference, in their entirety.

FIELD

The present disclosure relates to the medical equipment field, more particularly, to a retrievable puncture anchor.

BACKGROUND

At present, when diseases are treated through endoscopic surgery, tissues are often required to be connected, fixed and anastomosed, or required to be assisted and fixed, to facilitate surgical operation. For example, when cholecystolithotomy with gallbladder preserved, gastroenterostomy, or tissue dissection surgery is performed under an endoscope, tissues may often need to be anastomosed and fixed. However, there is no reliable instrument available in the market at present for performing the surgery.

The cholecystolithotomy with gallbladder preserved under endoscope is an operational method with great significance. The gallbladder stones may be removed endoscopically and gallbladder function may be preserved. The biggest problem currently encountered with such procedure is that the gallbladder may not be fixed, resulting in great operation difficulty and low success rate. Currently, there is no better solution.

It is common to perform a dissection operation of a diseased tissue using an endoscope. However, the biggest problem is that the tissue may not be fixed or moved, resulting in long operation time and great difficulty.

SUMMARY

The present disclosure is mainly aimed to provide a retrievable puncture anchor, which may be used to fix a gallbladder, or fix/move tissues during endoscopic surgery. Therefore, a tissue dissection surgery may be simple, and the puncture anchor may be retrieved after surgery.

In order to solve the technical problem, the technical solutions adopted by the present disclosure are as follows:

A retrievable puncture anchor is provided, which may include a fixator with a cylindrical structure, a retrievable thread fixed to an end of the fixator; and a push cable flexibly connected to a middle part of the fixator.

According to an embodiment of the present disclosure, the fixator may be axially provided with a slot and the push cable is flexibly connected in the slot.

According to an embodiment of the present disclosure, the middle part of the fixator may be provided with a threading hole in a radial direction of the fixator, and the push cable may pass through the threading hole.

According to an embodiment of the present disclosure, the fixator may be axially provided with a concave plane, and a threading protrusion may be formed on a side of the concave plane of the fixator. The threading protrusion may be axially provided with a through hole through which the push cable may be passed. The threading protrusion may be integrally formed with the fixator.

According to an embodiment of the present disclosure, one or both ends of the fixator may be spherically formed.

According to an embodiment of the present disclosure, the fixator may be formed from a rod or a tube.

According to an embodiment of the present disclosure, the push cable may be a hard thread and coated with a polymer material coating on a surface thereof, so as to reduce friction force during pushing.

According to an embodiment of the present disclosure, the push cable may be a soft thread, which is pushed together with other instrument.

According to an embodiment of the present disclosure, the retrievable thread may be a soft thread.

According to an embodiment of the present disclosure, the fixator may be made of hard material which has a certain rigidity and strength.

Advantageous effects: According to the retrievable puncture anchor of the present disclosure, tissues may be connected, fixed and matched with each other, or the tissues may be auxiliarily fixed, so that endoscopic surgery may be facilitated with simplified surgical process, and the puncture anchor may be retrieved or recycled after the surgery.

FIGURE NUMERALS

Figure 1:
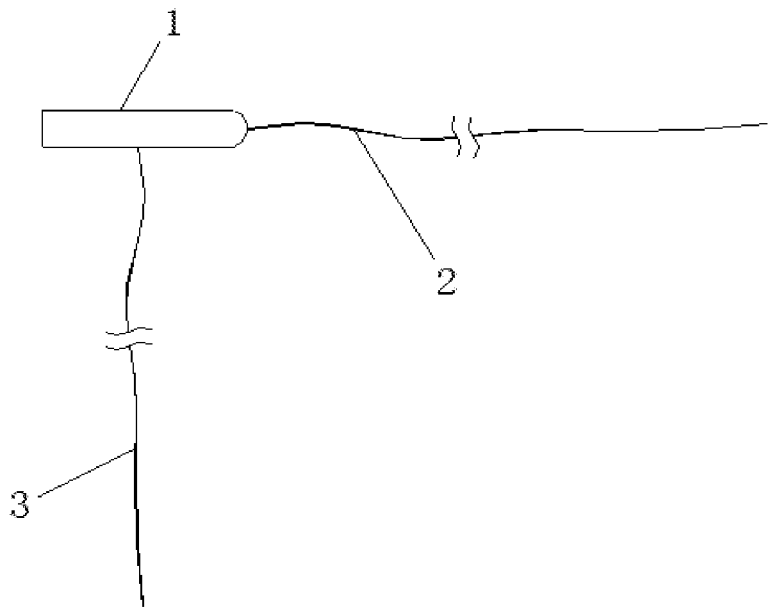
FIG. 1 is an overall schematic view of a retrievable puncture anchor according to an embodiment of the disclosure.

Fixator 1; retrievable thread 2; push cable 3; spherical structure 4; slot 5; threading hole 6; concave plane 7; threading protrusion 8; polymer material coating 9; puncture needle 10.

DETAILED DESCRIPTION

A retrievable puncture anchor according to an embodiment of the present disclosure will be described in further detail below with reference to the drawings.

As shown in FIG. 1, a retrievable puncture anchor may include a fixator 1, a retrievable thread 2 and a push cable 3. The fixator 1 may be of a cylindrical structure. The retrievable thread 2 may be fixed to an end of the fixator 1. The push cable 3 may be flexibly connected to the middle part of the fixator 1.

According to some embodiments of the present disclosure, the fixator 1 may be axially provided with a slot 5, and the push cable 3 may be flexibly connected in the slot 5. Therefore, the push cable 3 may be accommodated in the slot 5 when extending along an axial direction, so that the outer diameter of the whole puncture anchor may be not too large.

According to some embodiments of the present disclosure, the middle part of the fixator 1 may be provided with a threading hole 6 in a radial direction of the fixator 1. The push cable 3 may pass through the threading hole 6. When a plurality of puncture anchors need to be used, the push cable 3 only needs to pass through the threading holes 6 of the retrievable puncture anchors one by one in sequence, so as to connect the plurality of puncture anchors.

According to some embodiments of the present disclosure, the fixator 1 may be provided with a concave plane 7 along the axial direction. A threading protrusion 8 may be formed on the side of the concave plane 7 of the fixator 1. The threading protrusion 8 may be provided with a through hole 81 in the axial direction, and the push cable 3 may pass through the through hole 81. The threading protrusion 8 may be integrally formed with the fixator 1.

According to some embodiments of the present disclosure, one or both ends of the fixator 1 may be of a spherical structure 4. Due to being spherical, one end of the fixator 1 is safe and not sharp on one hand, and on the other hand, the center of the spherical structure is easy to be determined, so that the fixator 1 may be easy to be recovered. The spherical structure at the end of the fixator 1 in the present disclosure is not limited to one end.

According to some embodiments of the present disclosure, the fixator 1 may be formed from a rod or a tube.

Figure 5:
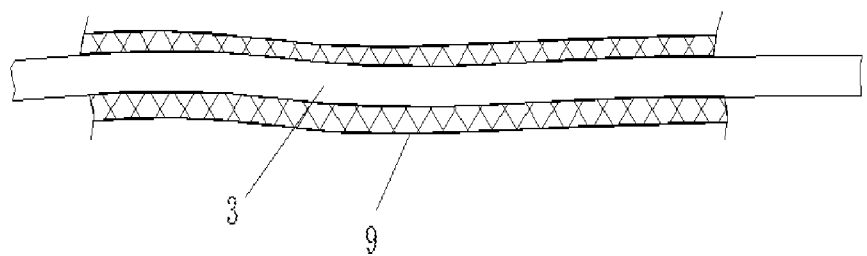
FIG. 5 is a schematic view of a push cable of a retrievable puncture anchor according to an embodiment of the disclosure.

According to some embodiments of the present disclosure, the push cable 3 may be a hard thread with certain push strength. The push cable may be coated with a polymer material coating 9 on the surface thereof, so as to reduce friction force during pushing, as shown in FIG. 5.

According to some embodiments of the present disclosure, the push cable 3 may be a soft thread, which is pushed together with other instruments. Pushing the push cable 3 together with other instruments in the present disclosure belongs to a conventional technical means, and will be not described in detail.

According to some embodiments of the present disclosure, the retrievable thread 2 may be a soft thread.

According to some embodiments of the present disclosure, the fixator 1 may be made of hard material which has a certain rigidity and strength.

Embodiment 1

Figure 2:
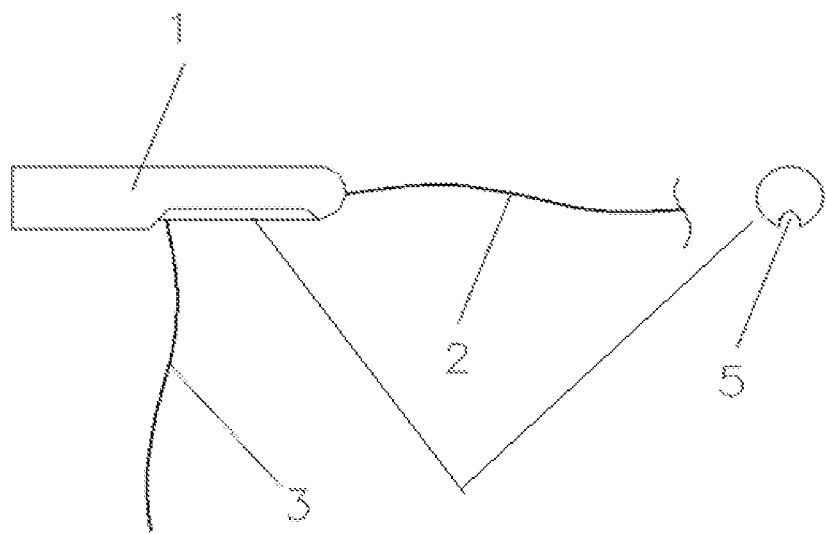
FIG. 2 is a schematic partial sectional view of a retrievable puncture anchor according to one embodiment of the disclosure.

As shown in FIG. 2, the fixator 1 may be of a cylindrical structure, with at least one end as a spherical structure 4. The retrievable thread 2 may be fixed at one end of the fixator 1. The slot 5 may be axially formed in the fixator 1. The push cable 3 may be flexibly connected to the middle part of the fixator 1, and located in the slot 5 which is used for accommodating the push cable 3. Therefore, when the push cable 3 is accommodated in the slot of the fixator 1 with the push cable 3 and the fixator 1 in a straight line, the outer diameter may be not increased, and the passing performance of the puncture anchor in the inner channel of the puncture needle 10 is improved.

Embodiment 2

Figure 3:
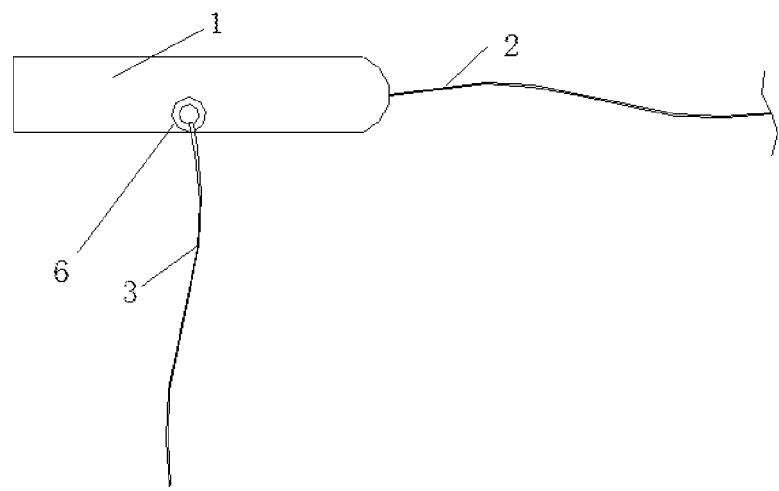
FIG. 3 is a schematic view of a retrievable puncture anchor according to another embodiment of the disclosure.

As shown in FIG. 3, the middle part of the fixator 1 may be provided with a threading hole 6 in a radial direction of the fixator 1. The push cable 3 may pass through the threading hole 6. The retrievable thread 2 may be fixed at one end of the fixator 1. The fixator 1 has at least one end being a spherical structure 4. Furthermore, the fixator 1 may be formed from a rod or tube. When a plurality of puncture anchors need to be used, the push cable 3 only needs to pass through the threading holes 6 of the retrievable puncture anchors one by one in sequence, so as to connect the plurality of puncture anchors.

Embodiment 3

Figure 4:
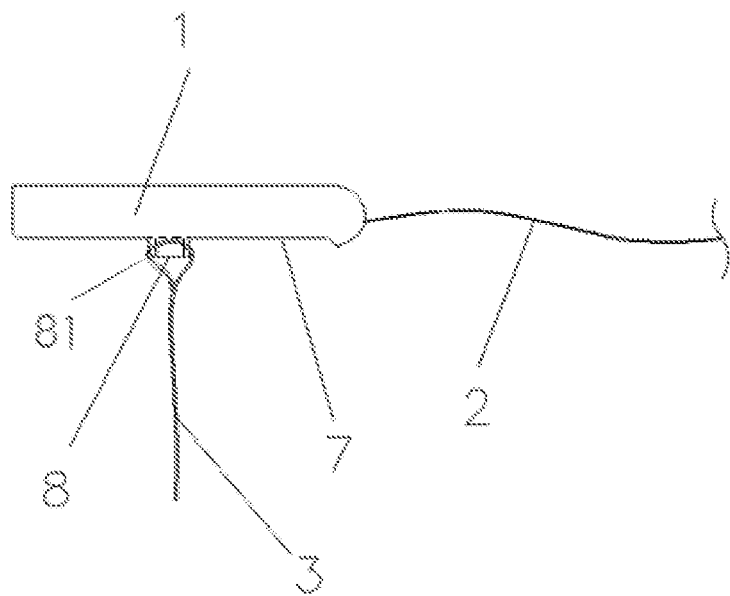
FIG. 4 is a schematic view of a retrievable puncture anchor according to a further embodiment of the disclosure.

As shown in FIG. 4, the fixator 1 may be provided with a concave plane 7 along the axial direction. A threading protrusion 8 may be formed on the side of the concave plane part 7 of the fixator 1. The threading protrusion 8 may be provided with a through hole 81 in the axial direction, and the push cable 3 may pass through the through hole 81. The threading protrusion 8 may be integrally formed with the fixator 1. Therefore, when the push cable 3 is accommodated in the slot of the fixator 1 with the push cable 3 and the fixator 1 in a straight line, the push cable 3 may be accommodated on the concave plane 7, so that the outer diameter of the puncture anchor may be not increased, and the passing performance of the puncture anchor in the inner channel of the puncture needle 10 is improved. The retrievable thread 2 may be fixed at one end of the fixator 1. The fixator 1 has at least one end being a spherical structure 4. Furthermore, the fixator 1 may be formed from a rod or a tube.

Figure 6:
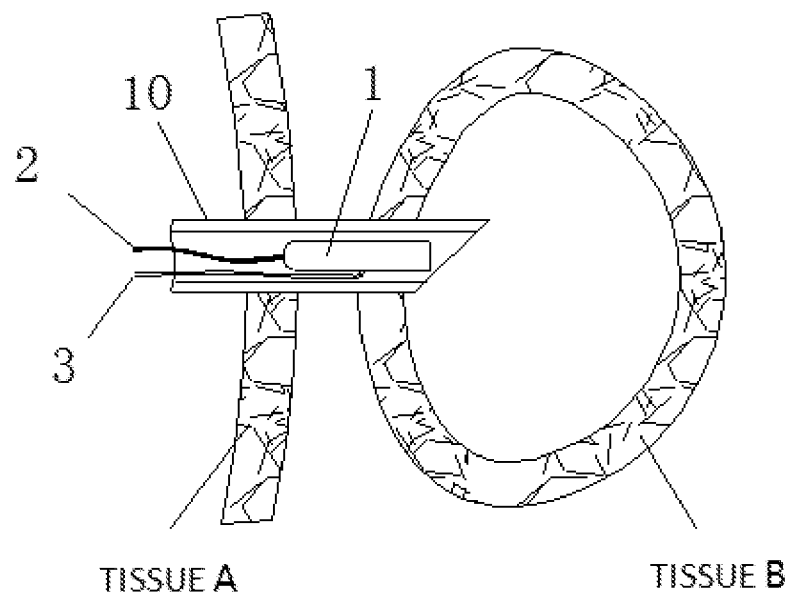
FIG. 6 is a schematic view of a retrievable puncture anchor penetrating into a puncture needle according to an embodiment of the disclosure.
Figure 7:
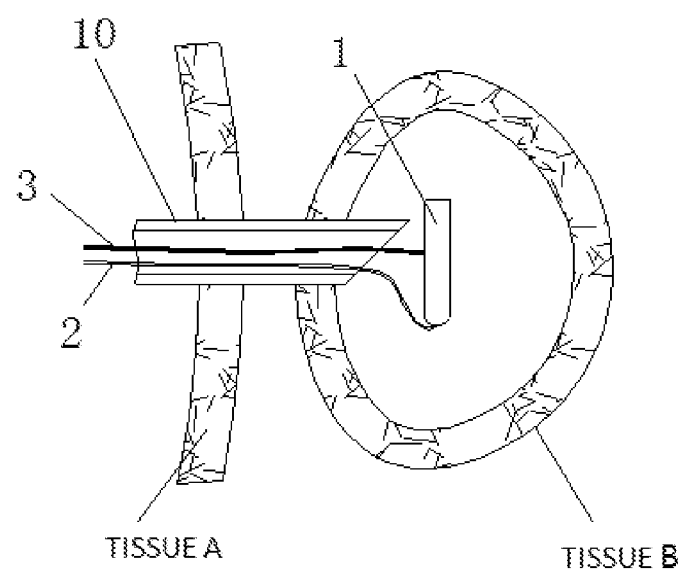
FIG. 7 is a schematic view of a retrievable puncture anchor puncturing out from a puncture needle according to an embodiment of the disclosure.
Figure 8:
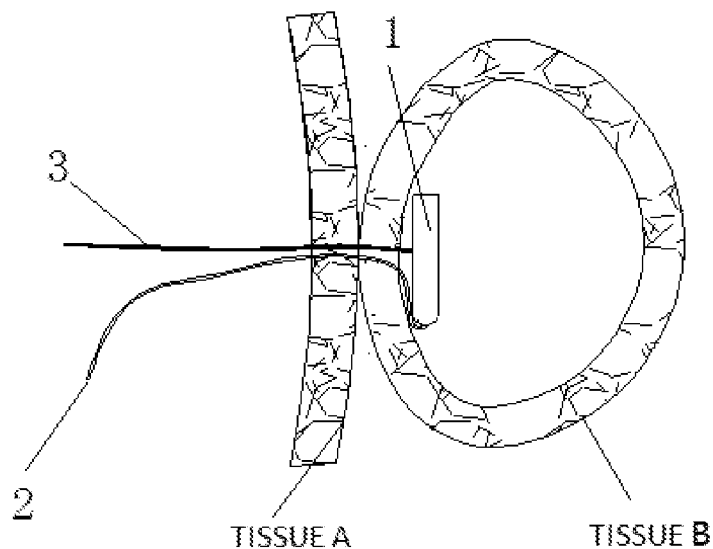
FIG. 8 is a schematic view of a retrievable puncture anchor joining tissue A and tissue B according to an embodiment of the disclosure.

The operation and use of the c retrievable puncture anchor according to embodiments of the present disclosure will be described below:

It is essentially the same for the use method of the Embodiments 1-3. As shown in FIG. 6, under the guidance of the endoscope, the endoscope puncture needle (or other similar instruments) may first puncture the tissue to the target position. Then the push cable 3 of the puncture anchor and the fixator 1 are arranged into a straight line (at this time, the push cable 3 may be located in the axial slot 5 of the fixator 1 in Embodiment 1, while the push cable 3 may be accommodated on the concave planar part 7). Next, as shown in FIG. 7, the fixator 1 may be pushed out of a needle end of the endoscope puncture needle 10 from the inner channel of the puncture needle 10 by using the push cable 3 (the end of the fixator 1 not connected with the retrievable thread 2 may enter the inner channel of the puncture needle 10 first). Afterward, the fixator 1 may be automatically perpendicular to the push cable 3. At this time, the tissues may be pulled and moved so as to close to each other, after the endoscope puncture needle is retrieved and the push cable 3 is pulled, as shown in FIG. 8. Of course, a target tissue may be moved independently, so that a convenient way may be provided for surgical treatment. After the operation is completed, the retrievable thread 2 may be pulled, and the fixator 1 may be automatically aligned with the retrievable thread 2. Therefore the puncture anchor may be finally retrieved.

The above embodiments are intended to describe the preferred embodiments of the present disclosure, but the present disclosure is not limited thereto, and various changes and modifications made to the technical solution and materials of the present invention by those skilled in the art without departing from the concept and working principle of the present disclosure should be protected by the claims of the present disclosure.

What is claimed is:

1. A retrievable puncture anchor, comprising:
a fixator with a cylindrical structure;
a retrievable thread fixed to an end of the fixator; and
a push cable flexibly connected to a middle part of the fixator,
wherein the fixator is axially provided with a concave plane, a threading protrusion is formed on a side of the concave plane of the fixator, the threading protrusion is axially provided with a through hole through which the push cable is passed, and the threading protrusion is integrally formed with the fixator.

2. The retrievable puncture anchor according to claim 1, wherein the fixator is axially provided with a slot, and the push cable is flexibly connected in the slot.

3. The retrievable puncture anchor according to claim 1, wherein the middle part of the fixator is provided with a threading hole in a radial direction of the fixator, and the push cable passes through the threading hole.

4. The retrievable puncture anchor according to claim 3, wherein the fixator is formed from a rod or a tube.

5. The retrievable puncture anchor according to claim 1, wherein one or both ends of the fixator is spherically formed.

6. The retrievable puncture anchor according to claim 5, wherein the push cable is a hard thread and coated with a polymer material coating on a surface thereof.

7. The retrievable puncture anchor according to claim 6, wherein the retrievable thread is a soft thread.

8. The retrievable puncture anchor according to claim 7, wherein the fixator is made of hard material.

9. The retrievable puncture anchor according to claim 5, wherein the push cable is a soft thread, which is pushed in cooperation with other instrument.

* * * * *